United States Patent [19]

Barnish et al.

[11] Patent Number: 5,260,467
[45] Date of Patent: Nov. 9, 1993

[54] GLUTARIC ACID DERIVATIVES AND PREPARATION THEREOF

[75] Inventors: Ian T. Barnish; Keith James, both of Kent, England

[73] Assignee: Pfizer Inc., New York, N.Y.

[21] Appl. No.: 28,854

[22] Filed: Mar. 10, 1993

Related U.S. Application Data

[62] Division of Ser. No. 882,785, May 14, 1992, which is a division of Ser. No. 757,853, Sep. 11, 1991, Pat. No. 5,157,138, which is a division of Ser. No. 604,845, Oct. 26, 1990, Pat. No. 5,087,732.

[30] Foreign Application Priority Data

Nov. 16, 1989 [GB] United Kingdom ............... 8925933

[51] Int. Cl.$^5$ ............... C07F 7/04; C07C 229/14
[52] U.S. Cl. ............... 556/418; 560/38
[58] Field of Search ............... 556/418; 560/38

[56] References Cited

U.S. PATENT DOCUMENTS 4,024,175  5/1977  Satzinger et al. ............... 260/468
5,030,654  7/1991  Barnish et al. ............... 514/510

FOREIGN PATENT DOCUMENTS 274234  7/1988  European Pat. Off.
358398  3/1990  European Pat. Off.

Primary Examiner—Jose G. Dees
Assistant Examiner—Joseph M. Conrad, III
Attorney, Agent, or Firm—Peter C. Richardson; Gregg C. Benson; Robert T. Ronau

[57] ABSTRACT

The invention provides the substantially optically pure 2(S)-stereoisomeric form of compounds of the formulae:

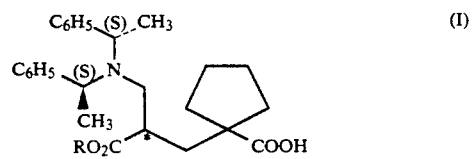

and

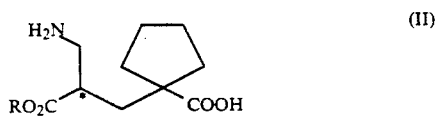

and the salts thereof, together with processes for their preparation. The compounds are intermediates for the preparation of antihypertensive agents.

1 Claim, No Drawings

GLUTARIC ACID DERIVATIVES AND PREPARATION THEREOF

This is a division of application Ser. No. 07/882,785, filed on May 14, 1992, which is a division of application Ser. No. 07/757,853, filed on Sep. 11, 1991, now U.S. Pat. No. 5,157,138 which is a division of application Ser. No. 07/604,845, filed on Oct. 26, 1990 (now U.S. Pat. No. 5,087,732, issued Feb. 11, 1992).

TECHNICAL FIELD

This invention relates to glutaric acid derivatives and processes for the preparation thereof.

More specifically the invention relates to the 2(S)-stereoisomeric form of 2-aminomethyl-3-(1-carboxycyclopentyl)propanoic acid derivatives and intermediates thereto, together with processes for the preparation thereof.

BACKGROUND ART

European Patent Application No. 89308740.3 discloses a series of cycloalkyl-substituted glutaramide derivatives which are antihypertensive agents having utility in the treatment of various cardiovascular disorders, including hypertension and heart failure, particularly preferred embodiments having the 2(S)- stereochemistry in the glutaramide fragment of the molecule. These compounds are prepared from optically pure precursors having the required 2(S)- stereochemistry, which may be obtained by fractional crystallisation of certain corresponding racemic (i.e. 2(R,S)-) intermediates.

SUMMARY OF THE INVENTION

The novel compounds provided in one aspect of the present invention may be usefully employed as intermediates for the preparation of certain preferred compounds disclosed in European Patent Application No. 89308740.3. New synthetic routes to these compounds are now available resulting in commercially important improvements over the existing processes such as ease and lower cost of operation.

The novel compounds of the present invention have been made available by the unexpected discovery that the required 2(S)- glutaric acid fragment may be generated at a comparatively early stage of the overall process by means of asymmetric synthesis. Thus a substantially pure 2(S)- stereoisomeric intermediate is generated in this process step, obviating the previous need for a fractional crystallisation stage to remove the corresponding, unwanted, 2(R)- stereoisomer.

One intermediate is the substantially optically pure 2(S)-stereoisomeric form of compounds having the formula:

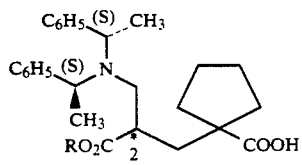

and acid addition salts and base salts thereof, wherein R is $C_1$-$C_4$ alkyl or —$CH_2CH_2Si(CH_3)_3$ and * indicates the asymmetric centre having (S)- stereochemistry.

Another intermediate is the substantially optically pure 2(S)-stereoisomeric form of compounds having the formula:

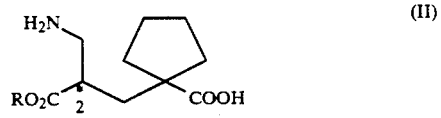

and acid addition salts and base salts thereof, wherein R and * are as defined for the formula (I).

Another aspect of this invention is a process for preparing a substantially optically pure 2(S)-stereoisomeric form of a compound of the formula (I), or an acid addition salt or base salt thereof, comprising the steps of:

i) reacting a compound of the formula:

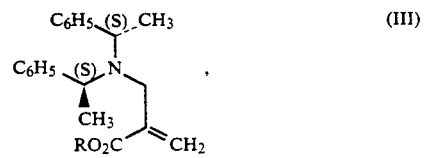

wherein R is as previously defined for the formula (I), with a salt of the formula:

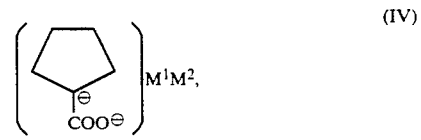

wherein $M^1$ and $M^2$, which may be the same or different, are selected from $Li^{\oplus}$, $Na^{\oplus}$ and $K^{\oplus}$, in an aprotic organic solvent at a temperature at or below $-10°$ C.; and ii) acidification of the reaction mixture at a temperature at or below $-10°$ C.; said process optionally being followed by conversion of the product of the formula (I) into an acid addition salt or a base salt thereof.

In the definition of the compounds of the formula (IV), preferably $M^1$ and $M^2$ are both $Li^{\oplus}$.

Yet another aspect of this invention is a process for preparing a substantially optically pure 2(S)-stereoisomeric form of a compound of the formula (II), or an acid addition salt or a base salt thereof, which comprises catalytic hydrogenation of a substantially optically pure 2(S)-stereoisomeric form of a compound of the formula (I), or an acid addition salt or a base salt thereof; said process optionally being followed by conversion of the product of the formula (II) into an addition salt or a base salt thereof.

In the formulae (I) and (III) above, the substituent "$C_6H_5$" represents phenyl.

Alkyl groups containing three or four carbon atoms may be straight or branched chain.

In the above definitions of the compounds of the formulae (I), (II) and (III), preferably R is $C_1$-$C_4$ alkyl.

Most preferably R is methyl, ethyl or t-butyl.

The term "substantially optically pure" means that the compounds of the formulae (I) and (II), and acid addition salts and base salts thereof, contain less than 10%, and preferably less than 5%, of the 2(R)-stereoisomer.

Examples of suitable acid addition salts of compounds of the formulae (I) and (II) include the hydrochloride, hydrobromide, hydroiodide, sulphate or bisulphate, phosphate or hydrogen phosphate, acetate, maleate, fumarate, lactate, tartrate, citrate, gluconate, benzoate, methanesulphonate, benzenesulphonate and p-toluenesulphonate salts.

Examples of suitable base salts of compounds of the formulae (I) and (II) include alkali metal, alkaline earth metal, trialkylammonium and N-alkylmorpholinium salts.

The preferred base salt of the compounds of the formulae (I) and (II) is the sodium salt.

DETAILED DESCRIPTION OF THE INVENTION

1. A substantially optically pure 2(S)-stereoisomeric form of a compound of the formula (I) is prepared by an asymmetric synthesis in which, typically, the salt (IV) may be generated either by deprotonation of cyclopentanecarboxylic acid in situ using at least two equivalents of a suitable strong base, or by deprotonation of a suitable base salt of cyclopentanecarboxylic acid, e.g. lithium, sodium or potassium cyclopentanecarboxylate, using at least one equivalent of a suitable strong base.

Examples of a suitable strong base for these purposes are potassium diisopropylamide, lithium hexamethyldisilazide and, preferably, lithium diisopropylamide.

In a preferred procedure, the salt (IV) is generated by the deprotonation of cyclopentanecarboxylic acid in situ using at least two equivalents of lithium diisopropylamide. The deprotonation is carried out under an inert atmosphere at a temperature at from −70° C. to room temperature and in a suitable aprotic organic solvent, e.g. tetrahydrofuran. The acrylate (III) is then reacted with the salt (IV) at an initial temperature at from −80° C. to −10° C., preferably at from −70° C. to −15° C. and, after a period of stirring at about −15° C., the reaction is quenched by acidification.

Acidification is preferably carried out by pouring the reaction mixture at a temperature of about −15° C. into an ice-cooled aqueous solution of a suitable acid.

Any suitable mineral or organic acid may be used in the acidification step such as hydrochloric, sulphuric, citric or acetic acid. Most preferably hydrochloric acid is used.

The product of the formula (I) may then be isolated and purified by conventional techniques, e.g. by extractive work-up and/or chromatography.

This procedure unexpectedly yields the product of the formula (I) having the 2(S)-stereochemistry in high optical purity, typically containing less than or equal to 5% of the corresponding 2(R)-stereoisomer.

The starting materials of the formula (III) required for the preparation of compounds of the formula (I) may be prepared by conventional procedures as illustrated by Scheme 1:

Scheme 1

Br—C(=CH₂)—CO₂R
(V)

+

-continued
Scheme 1

C₆H₅·(S)·CH₃
  |
C₆H₅·(S)·NH     →  K₂CO₃/CH₃CN
  |
  CH₃

(VI)

C₆H₅·(S)·CH₃
  |
C₆H₅·(S)·N
  |   \
  CH₃  CH₂—C(=CH₂)—CO₂R (III)

wherein R is as previously defined for the formula (I).

In a typical procedure (S,S)-α, α′-dimethyldibenzylamine (VI) is added to a cooled mixture of the 2-bromomethylpropenoate (V) and potassium carbonate in acetonitrile. The mixture is heated at about 60° C. for about 18 hours and the acrylate (III) is then isolated by conventional techniques.

2-Bromomethylpropenoates of the formula (V) are either commercially available or prepared by standard techniques.

The chiral auxiliary of the formula (VI) may be prepared by the method of C. G. Overberger, N. P. Marullo and R. G. Hiskey, J.A.C.S., 83, 1374 (1961).

A substantially optically pure 2(S)-stereoisomeric form of a compound of the formula (II) may be prepared by catalytic hydrogenation of the corresponding substantially optically pure 2(S)-stereoisomeric form of a compound of the formula (I), or an acid addition salt or base salt thereof. This has the effect of deprotecting the amino substituent by removing the α-methylbenzyl groups introduced via the chiral auxiliary, thus producing a more versatile synthetic intermediate (II).

The catalytic hydrogenation is most preferably carried out on a suitable base salt of the compound of the formula (I) in order to minimise or avoid the possibility of concomitant δ-lactam formation after deprotection of the amino function. For this reason also compound (II) is preferably isolated and stored in the form of a suitable base salt.

In a typical procedure compound (I) is first converted to a suitable base salt, e.g. an alkali metal, alkaline earth metal, trialkylammonium or N-alkylmorpholinium salt, and then reduced by catalytic hydrogenation in a suitable solvent, e.g. a $C_1$–$C_4$ alkanol or an aqueous solution thereof.

The catalytic hydrogenation is preferably carried out on the sodium salt of compound (I) using a palladium hydroxide-on-charcoal catalyst at room temperature in ethanol.

The base salt of the product of the formula (II) may then be isolated and purified by conventional techniques.

A compound of the formula (I) or (II) may be converted into an acid addition salt or base salt thereof by mixing together solutions containing equimolar amounts of the appropriate compound and a suitable acid or base, as required. The salt may precipitate from the solution and is collected by filtration or it may be recovered by evaporation of the solvent.

The compounds of the formulae (I) and (II), and acid addition salts and base salts thereof, provided by the invention may be used to prepare certain preferred compounds disclosed in European Patent Application No. 89308740.3 for example by (i) converting a compound of the formula (I), or an acid addition salt or a base salt thereof, to an appropriate glutaramide derivative, deprotecting the amino function by catalytic hydrogenation and reacting the resulting primary amino group with an appropriate lysine derivative; and (ii) reacting the amino function of a base salt of a compound of the formula (II) with an appropriate lysine derivative followed by formation of an appropriate glutaramide derivative.

The following Examples illustrate the invention:

EXAMPLE 1

2(S)-Aminomethyl-3-(1-carboxycyclopentyl)propanoic acid t-butyl ester, sodium salt, hemihydrate

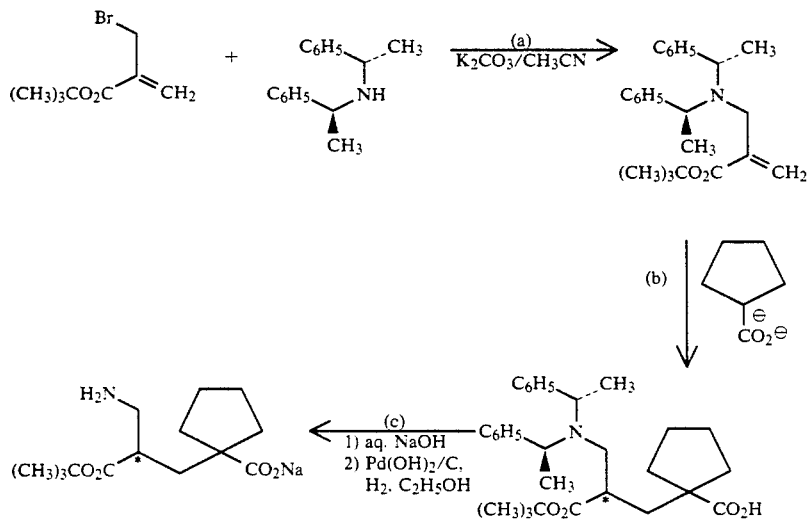

(a)
2-[(S,S)-α,α'-Dimethyldibenzyl]aminomethylpropenoic acid t-butyl ester

To a stirred, ice-cooled solution of 2-(bromomethyl)-propenoic acid t-butyl ester (29.4 g, 0.133 mol) in acetonitrile (150 ml) was added anhydrous potassium carbonate (22.9 g, 0.166 mol), followed by dropwise addition of a solution of (S,S)-α,α'-dimethyldibenzylamine (34.3 g, 0.152 mol) (see C. G. Overberger et. al., J.A.C.S., 83, 1374 (1961)) in acetonitrile (150 ml). The resulting mixture was stirred at 60° C. for 18 hours then evaporated in vacuo. The residue was partitioned between diethyl ether (200 ml) and water (100 ml), the ether phase separated, and the aqueous phase further extracted with diethyl ether (3×200 ml).

The combined ether extracts were washed with water (5×100 ml), dried (anhydrous magnesium sulphate), filtered and evaporated in vacuo to give a pale yellow oil. This was purified by chromatography on silica gel using a 0–2% ethyl acetate in hexane elution gradient. Combination and evaporation in vacuo of the appropriate fractions provided the required product (40.5 g, 83%), $[\alpha]_{589}^{25} -59.3°$ (c=1, methanol). Found: C,78.63; H,8.58; N,3.59; $C_{24}H_{31}NO_2$ requires: C,78.86; H,8.55; N,3.83%.

(b)
2(S)-[(S,S)-α,α'-Dimethyldibenzyl]aminomethyl-3-(1-carboxycyclopentyl)propanoic acid t-butyl ester, monohydrate A solution of n-butyllithium in hexane (2.5M, 34.4 ml, 0.086 mol) was added dropwise, under dry nitrogen, to a stirred solution of diisopropylamine (8.70 g, 0.086 mol) in dry tetrahydrofuran (200 ml) at −30° C. The resulting solution was allowed to warm to 0° C. for 15 minutes then recooled to −40° C. before the dropwise addition of a solution of cyclopentanecarboxylic acid (4.68 g, 0.041 mol) in dry tetrahydrofuran (65 ml). The reaction mixture was stirred at room temperature for 2 hours then cooled to −70° C. A solution of the product of part (a) (15.0 g, 0.041 mol) in dry tetrahydrofuran (35 ml) was added dropwise to the mixture containing the dianion, the reaction temperature maintained at −70° C. for a further 30 minutes then allowed to warm to −15° C. and kept at −15° C. for 2 hours.

The resulting pale yellow solution was poured into a stirred, ice-cooled mixture of 1M hydrochloric acid (200 ml) and diethyl ether (200 ml). The ether phase was separated and the aqueous phase further extracted with diethyl ether (3×200 ml). The combined ether extracts were washed successively with saturated aqueous sodium bicarbonate solution (5×100 ml), water (2×200 ml) and saturated brine (2×200 ml) then dried (anhydrous magnesium sulphate). The organic extracts were filtered and evaporated in vacuo to provide a yellow oil which was purified by chromatography on silica gel using a 0–25% ethyl acetate in hexane elution gradient. Combination and evaporation in vacuo of the appropriate fractions afforded the required product (16.3 g, 80%), $[\alpha]_{589}^{25} -19.9°$ (c=1, methanol). Found: C,72.62; H,8.48; N,2.79; $C_{30}H_{41}NO_4.H_2O$ requires: C,72.40; H,8.71; N,2.81%.

$^1$H-NMR (300 MHz) spectroscopy showed the product to be approximately 95% optically pure in respect of the required 2(S)-stereoisomer.

(c)
2(S)-Aminomethyl-3-(1-carboxycyclopentyl)propanoic acid t-butyl ester, sodium salt, hemihydrate A solution of the product of part (b) (10.0 g, 0.020 mol) in ethanol (100 ml) was treated with an aqueous solution of sodium hydroxide (1M, 19.9 ml) and the resulting solution evaporated under high vacuum at room temperature. A gum was obtained which was dissolved in ethanol (150 ml) and hydrogenated over 20% palladium hydroxide-on-charcoal (1.0 g) at 60 p.s.i. (414 kPa) and room temperature for 18 hours. The catalyst was removed by filtration through a pad composed of proprietory cellulose-based filter aids and the filtrate was evaporated under high vacuum at room temperature. The residual solvents were removed azeotropically with dichloromethane (3×50 ml) to provide the required product as a white, waxy solid (5.79 g, 95%), $[\alpha]_{589}^{25} -3.0°$ (c=1, methanol). Found: C,55.81; H,8.28; N,4.34; $C_{14}H_{24}NO_4Na$. 0.5 $H_2O$ requires: C,55.61; H,8.33; N,4.63%.

EXAMPLE 2

2(S)-[(S,S)-α,α'-Dimethyldibenzyl]aminomethyl-3-(1-carboxycyclopentyl)propanoic acid ethyl ester (a)

2-[(S,S)-α,α'-Dimethyldibenzyl]aminomethylpropenoic acid ethyl ester

The synthesis was effected as in Example 1(a) using a solution of 2-(bromomethyl)propenoic acid ethyl ester (10.0 g, 0.052 mol) in acetonitrile (60 ml), anhydrous potassium carbonate (8.9 g, 0.065 mol) and a solution of (S,S)-α,α'-dimethyldibenzylamine (12.8 g, 0.057 mol) in acetonitrile (40 ml).

The crude oil obtained was purified by chromatography on silica gel using a 0-10% ethyl acetate in hexane elution gradient to afford, after combination and evaporation of the appropriate fractions, the required product (16.8 g, 96%), $[\alpha]_{589}^{25} -62.5°$ (c=1, methanol). Found: C,78.25; H,8.10; N,4.29; $C_{22}H_{27}NO_2$ requires: C,78.30; H,8.07; N,4.15%.

(b)

2(S)-[(S,S)-α,α'-Dimethyldibenzyl]aminomethyl-3-(1-carboxycyclopentyl)propanoic acid ethyl ester The synthesis was effected as in Example 1(b) using a solution of n-butyllithium in hexane (2.5M, 17.4 ml, 0.0435 mol), a solution of diisopropylamine (4.4 g, 0.0435 mol) in dry tetrahydrofuran (100 ml), a solution of cyclopentanecarboxylic acid (2.41 g, 0.021 mol) in dry tetrahydrofuran (35 ml) and a solution of the product of part (a) (7.0 g, 0.021 mol) in dry tetrahydrofuran (15 ml).

The crude gum obtained was purified by chromatography on silica gel using a 0-10% ethyl acetate in hexane elution gradient to provide, after combination and evaporation of the appropriate fractions, the required product (4.9 g, 52%), $[\alpha]_{589}^{25} -13.2°$ (c=1, methanol). Found: C,74.16; H,8.18; N,3.27; $C_{28}H_{37}NO_4$ requires: C,74.47; H,8.26; N,3.10%.

$^1$H-NMR (300 MHz) spectroscopy showed the product to be approximately 95% optically pure in respect of the required 2(S)-stereoisomer.

EXAMPLE 3

2(S)-[(S,S)-α,α'-Dimethyldibenzyl]aminomethyl-3-(1-carboxycyclopentyl)propanoic acid methyl ester (a)

2-[(S,S)-α,α'-Dimethyldibenzyl]aminomethylpropenoic acid methyl ester

The synthesis was effected as in Example 1(a) using a solution of 2-(bromomethyl)propenoic acid methyl ester (5.8 g, 0.032 mol) in acetonitrile (40 ml), anhydrous potassium carbonate (5.52 g, 0.040 mol) and a solution of (S,S)-α,α'-dimethyldibenzylamine (8.1 g, 0.036 mol) in acetonitrile (40 ml).

The crude oil obtained was purified by chromatography on silica gel using a 0-10% ethyl acetate in hexane elution gradient to provide, after combination and evaporation of the appropriate fractions, the required product (9.7 g, 94%), $[\alpha]_{589}^{25} -69.7°$ (c=1, methanol). Found: C,78.19; H,8.00; N,4.45; $C_{21}H_{25}NO_2$ requires: C,77.99; N,7.91; N,4.33%.

(b)

2(S)-[(S,S)-α,α'-Dimethyldibenzyl]aminomethyl-3-(1-carboxycyclopentyl)propanoic acid methyl ester The synthesis was effected as in Example 1(b) using a solution of n-butyllithium in hexane (2.5M, 17.4 ml, 0.0435 mol), a solution of diisopropylamine (4.4 g, 0.0435 mol) in dry tetrahydrofuran (100 ml), a solution of cyclopentanecarboxylic acid (2.41 g, 0.021 mol) in dry tetrahydrofuran (35 ml) and a solution of the product of part (a) (6.79 g, 0.021 mol) in dry tetrahydrofuran (15 ml).

The crude oil obtained was purified by chromatography on silica gel using a 0-30% ethyl acetate in hexane elution gradient to provide, after combination and evaporation of the appropriate fractions, the required product (7.77 g, 84%), $[\alpha]_{589}^{25} -10.8°$ (c=1, methanol). Found: C,73.61; H,8.01; N,3,21; $C_{27}H_{35}NO_4$ requires: C,74.12; H,8.06; N,3.20%.

$^1$H-NMR (300 MHz) spectroscopy showed the product to be approximately 95% optically pure in respect of the required 2(S)-stereoisomer.

We claim:

1. A compound of the formula (III)

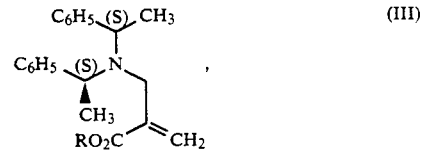

wherein R is —$(C_1-C_4)$alkyl or —$CH_2CH_2Si(CH_3)_3$.

* * * * *